United States Patent [19]

Talonn et al.

[11] Patent Number: 5,053,018
[45] Date of Patent: Oct. 1, 1991

[54] COMBINED SYRINGE AND NEEDLE SHIELD AND METHOD OF MANUFACTURE

[75] Inventors: Daniel A. Talonn, University City; Alan B. Ranford, St. Louis, both of Mo.

[73] Assignee: Sherwood Medical Company, St. Louis, Mo.

[21] Appl. No.: 212,528

[22] Filed: Jun. 28, 1988

[51] Int. Cl.⁵ ............................................. A61M 5/32
[52] U.S. Cl. ................................. 604/198; 604/110; 604/263; 604/192; 128/919; 128/763
[58] Field of Search ............... 604/192, 197, 198, 263, 604/110; 128/763, 770

[56] References Cited

U.S. PATENT DOCUMENTS

| | | |
|---|---|---|
| 2,571,653 | 10/1951 | Bastien . |
| 3,780,734 | 12/1973 | Wulff . |
| 3,890,971 | 6/1975 | Leeson et al. . |
| 4,170,993 | 10/1979 | Alvarez . |
| 4,356,822 | 11/1982 | Winstead-Hall . |
| 4,425,120 | 1/1984 | Sampson et al. . |
| 4,573,967 | 3/1986 | Sampson et al. . |
| 4,631,057 | 12/1986 | Mitchell . |
| 4,643,199 | 2/1987 | Jennings, Jr. et al. . |
| 4,643,200 | 2/1987 | Jennings, Jr. . |
| 4,650,468 | 3/1987 | Jennings, Jr. . |
| 4,655,751 | 4/1987 | Harbaugh . |
| 4,666,435 | 5/1987 | Braginetz . |
| 4,681,567 | 7/1987 | Masters et al. . |
| 4,693,708 | 9/1987 | Wanderer et al. . |
| 4,695,274 | 9/1987 | Fox . |
| 4,702,739 | 10/1987 | Milurad ................................ 604/198 |
| 4,723,943 | 2/1988 | Spencer . |
| 4,737,144 | 4/1988 | Choksi . |
| 4,743,233 | 5/1988 | Schneider ........................... 604/192 |
| 4,747,837 | 5/1988 | Hauck ................................. 604/198 |
| 4,758,231 | 7/1988 | Haber et al. ........................ 604/198 |
| 4,840,185 | 6/1989 | Hernandez .......................... 128/763 |
| 4,842,587 | 6/1989 | Poncy ................................. 604/198 |
| 4,850,994 | 7/1989 | Zerbst et al. ........................ 604/198 |
| 4,874,383 | 10/1989 | McNaughton ....................... 604/198 |
| 4,923,445 | 5/1990 | Ryan .................................. 604/195 |
| 4,927,018 | 5/1990 | Yang et al. .......................... 206/365 |

FOREIGN PATENT DOCUMENTS

| | | |
|---|---|---|
| A1216460 | 4/1987 | European Pat. Off. . |
| A2240987 | 10/1987 | European Pat. Off. . |
| A1250104 | 12/1987 | European Pat. Off. . |
| A2252644 | 1/1988 | European Pat. Off. . |
| 2833804 | 3/1979 | Fed. Rep. of Germany . |
| 8606355 | 10/1986 | Fed. Rep. of Germany . |
| 3609516 | 6/1987 | Fed. Rep. of Germany . |

*Primary Examiner*—C. Fred Rosenbaum
*Assistant Examiner*—Mark O. Polutta
*Attorney, Agent, or Firm*—Andrew J. Beck; Montgomery W. Smith; Richard D. Allison

[57] ABSTRACT

A safety syringe including a needle shield which is movable between a retracted position wherein protected. The needle shield is also rotatable in either direction from the releasable extended position to a locked and extended position. A collar having a plurality of protrusions and locking slots thereon is mounted on the distal end of the syringe to interact with a plurality of elongate keys which extend inwardly from the interior surface of the needle shield.

30 Claims, 3 Drawing Sheets

COMBINED SYRINGE AND NEEDLE SHIELD AND METHOD OF MANUFACTURE

This invention relates to syringes and, in particular, to a hypodermic syringe having a retractable needle guard primarily for the purpose of preventing accidental needle sticks.

Most syringes used today for medical or laboratory purposes are sold as disposable items intended to be used only once. Disposal of such syringes has posed a safety hazard for the individuals who use the syringes as well as for those who dispose of them. With the onset of AIDS, the concern for infection due to accidental needle sticks from used syringes has increased and a number of different devices have been proposed to minimize the possibility of spreading infectious disease due to accidents of this type.

One approach to this problem is to provide a retractable shield which, after the syringe has been used, can be pulled to an extended position where it covers the needle, making it difficult for an individual to accidentally contact the needle. A common feature of such constructions is that when the shield is pulled to its extended position, it is locked so that it cannot be retracted (thus exposing the needle) except by application of extraordinary force.

A number of such constructions have been proposed to satisfy the general requirement that the needle be permanently covered after the syringe has been used. Some of these constructions involve twist-to-lock mechanisms and, in others, locking occurs automatically when the shield is fully extended. These known devices satisfy many of the functional requirements of a needle shield but require, in most cases, modification of the standard syringe construction. This is highly undesirable for some manufacturers because of the sizable investment they may have already made in their existing molding equipment for producing the syringes.

Moreover, certain operational problems arise when a shield is incorporated into a syringe. For example, since the shield, when it is retracted, essentially covers the barrel of the syringe, it is desirable to be able to insert and remove a needle while holding onto the shield alone. This involves twisting and pushing (or pulling) the needle to place it on (or remove it from) the luer and can be awkward with some known constructions.

Further, constructions have been proposed which include an opening or slot in the side of the shield. This is undesirable because the needle can extend through the opening if the shield is deflected in the extended position.

Those devices which lock in response to axial movement to the extended position, (i.e., without any rotation) have certain inherent drawbacks that result primarily from the requirement that substantial force be exerted axially to lock the shield in its extended position. In the first place, the likelihood of unintentional and irreversible locking is greater with such devices than with those devices which require rotation to lock. Also, it is difficult to verify that the shield is locked upon such forcible extension without attempting to retract the shield, which increases the possibility of unintended exposure of the needle. Finally, if the user's hand should slip from the shield while exerting the force necessary to extend the shield to the locked position, the user's hand may reflexively rebound back onto the needle point if the shield does not actually lock.

Other proposed devices have included open ended shields which would not block access to the needle point by small fingers.

Accordingly, it is an object of this invention to provide a protective shield of the type described which can be added at minimal expense to standard syringes.

Another object of the invention is to provide a relatively inexpensive protective shield which satisfies the functional requirements of a needle shield and includes none of the drawbacks mentioned above.

Another object is to provide an extendable needle shield for a syringe which performs all of the necessary functions of such a shield and which is particularly well suited to an automated process of manufacture.

A further object of the invention is to provide an extendable needle shield for a standard syringe which is improved both from the points of view of functional utility and cost of manufacture.

A still further object is to provide an inexpensive method of assembling a protective shield and syringe.

SUMMARY OF THE INVENTION

In accordance with the invention, a needle shield is mounted coaxially on a syringe barrel. The shield includes one or more elongated keys on its inner surface. A collar is provided on the forward end of the barrel. The collar may be a separate part or it may be integrally formed with the barrel and includes on its outer surface at least one locking slot. The key slides in a path outside of the locking slot and can be rotated into the locking slot when the shield is extended. Both the collar and shield can be molded from plastic materials so that the cost of the shield is relatively low.

In a preferred embodiment, the shield includes a plurality of elongated locking keys and the collar includes a plurality of locking slots. Each locking slot is defined by opposing walls, at least one of which includes a ramp over which the keys can ride when the shield is pulled to its extended position and rotated.

In the preferred embodiment, when the keys are rotated into the locking slots, rearward movement of the shield to its retracted position is prevented by a surface on the collar at the back of each locking slot. In accordance with a further feature of the invention, protrusions on the collar and the forward portions of the keys are shaped such that during assembly the keys are directed into keyways formed between the locking slots as the collar is moved relative to the shield. Thus, the construction is well suited to an automated process in which the collar and shield are secured to the syringe by machine.

Other benefits of the invention are set forth below in the detailed description which follows:

IN THE DRAWINGS

FIG. 1 is a side elevational view, partly in section, showing a needle shield and collar in accordance with a preferred embodiment of the invention secured to a conventional syringe with the shield in its retracted position;

FIG. 2 is an enlarged sectional view with the shield in cross-section in its extended position;

DETAILED DESCRIPTION

In its preferred embodiment, the invention is intended to be used in conjunction with a conventional syringe; however, a protective shield in accordance with the invention can be used for any medical or laboratory device having a needle, such as a blood collection tube holder with a double ended needle. Accordingly, as used herein, the term "syringe" is intended to include any medical or scientific device including a needle wherein it is desired to protect a user from accidental needle sticks.

In describing the invention, the "distal end" of a part refers to the end of the part closest to the needle point. The "proximal end" of a part refers to the end furthest from the needle point.

Figure 8:
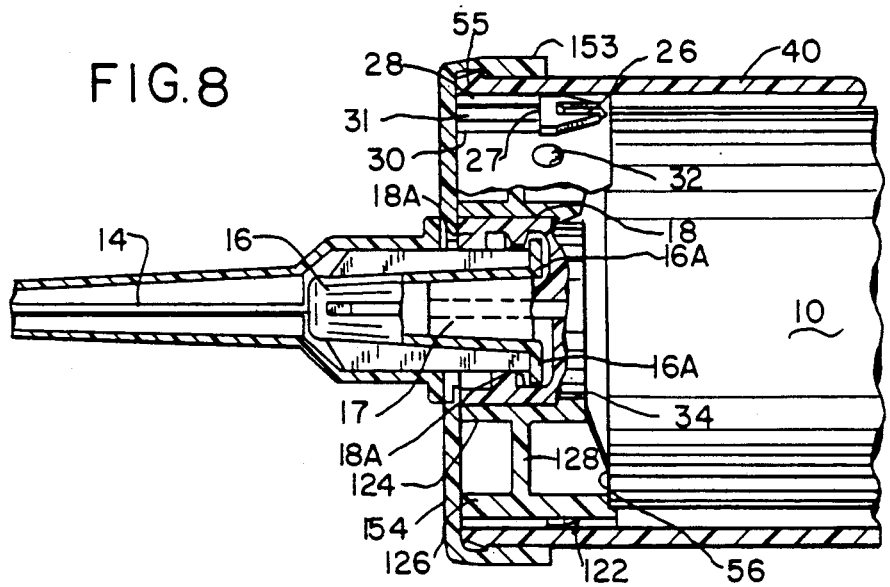
FIG. 8 is a side sectional view showing a collar construction for use with a large diameter barrel.

FIGS. 1-6 show a conventional syringe comprising a tubular barrel 10 having a finger flange 11, a plunger 12 slidable within the barrel 10, and a needle assembly through which the contents of the barrel are dispensed when the plunger 12 is depressed. The barrel 10 may be tapered very slightly (not shown) from a larger diameter proximal end to a smaller diameter distal end for molding purposes. The needle assembly comprises a needle 14 and a hub 16 at the proximal end of the needle. As is standard, a conically shaped luer tip 17 and luer lock skirt 18 are integrally formed at the distal end of barrel 10 with luer lock skirt 18 encircling luer tip 17. As shown in FIG. 8 (directed to a different collar construction and described in detail below), the interior surface of the luer lock skirt 18 includes an internal thread 18A adapted to threadably engage complementary locking ears 16A on the needle hub 16. The exterior surface of luer lock skirt 18 includes a multiplicity of ribs 19 parallel to the central axis of the barrel. The needle and luer arrangement of FIG. 8 is the same as that of FIGS. 1-6.

A needle sheath 20 covers needle 14 as a protective device. Sheath 20 frictionally engages hub 16 and can be used to disconnect the needle assembly from the luer lock skirt 18 in conventional fashion.

The construction as so far described is that of a standard disposable syringe and forms no part of the invention.

Figures 1, 2:
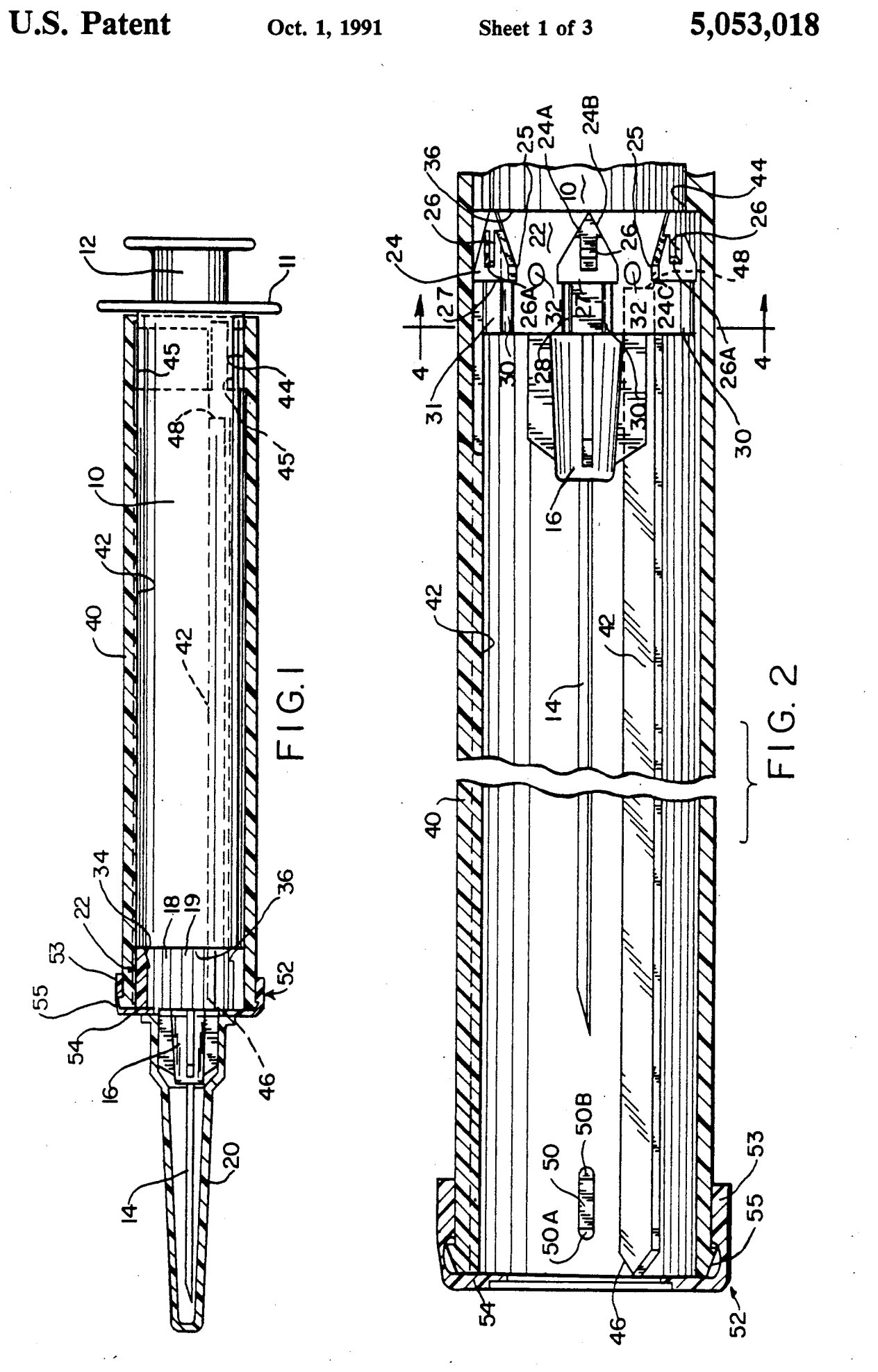
Figure 6:
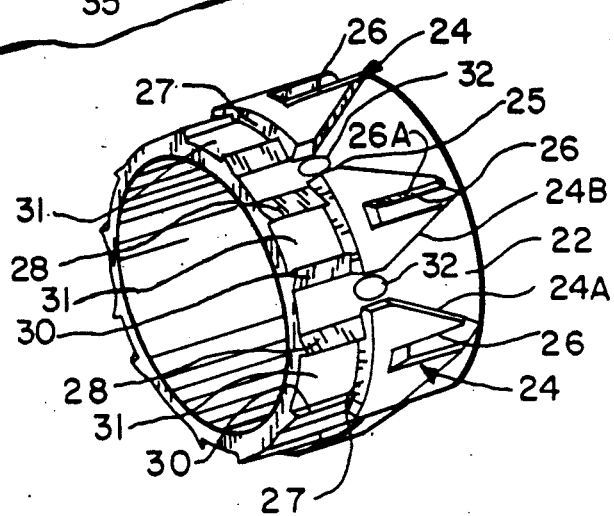
FIGS. 6 and 7 are perspective views of a preferred embodiment of the collar.

The collar employed in accordance with the preferred embodiment of the invention is shown generally at 22 (FIGS. 2, 6 and 8). As mentioned above, although collar 22 is shown as a separate piece, the collar (or its functional equivalent) may be integrally formed as a part of the barrel 10. It includes six equally spaced and integrally formed identical triangular protrusions 24, with the apex of each protrusion extending away from the needle. Keyways 25 are formed between each adjacent pair of protrusions 24.

The triangular protrusions 24 each include angled surfaces 24A and 24B, side surfaces 25C, a slot 26 and a surface 27 which is generally circumferential and functions as a stop as explained below. The slot 26 includes a sloped distal surface 26A. It is not necessary that protrusions 24 be triangular in shape and other configurations can be used to provide a stop 27 for the keys and the angled surfaces 25A and 25B necessary to guide the keys into the keyways during the assembly process as described below. The slot 26 is formed in protrusion 24 and extends proximally to the point of the protrusion 24 to expose the detenting surface 26A and facilitate the entry of the detent 50 into the slot 26 during assembly, and also to facilitate efficient molding of the collar. At the forward end of each protrusion, two walls 28 and 30 extend toward the needle. A rectangular locking slot 31 is formed between each pair of walls 28 and 30, which are ramp shaped in cross section as shown most clearly in FIGS. 4, 5 and 6. As shown in FIGS. 3, 4, 5 and 6, the surface of locking slot 31 is slightly elevated relative to the level of the keyways 25, i.e., the collar diameter at the locking slots 31 is slightly greater than the collar diameter at the keyways. The slight increase in the collar diameter at the locking slots removes some of the slack between the needle shield (described below) and the collar 22 resulting from the slight taper of the barrel 10 in the preferred embodiment. This prevents or at least minimizes wobble or play of the shield when it is locked in the extended position. A circular detent 32 is positioned between each pair of triangular protrusions 24 with the forward points of detents 32 lying just in front of the bases of triangular projections 24.

Figure 3:
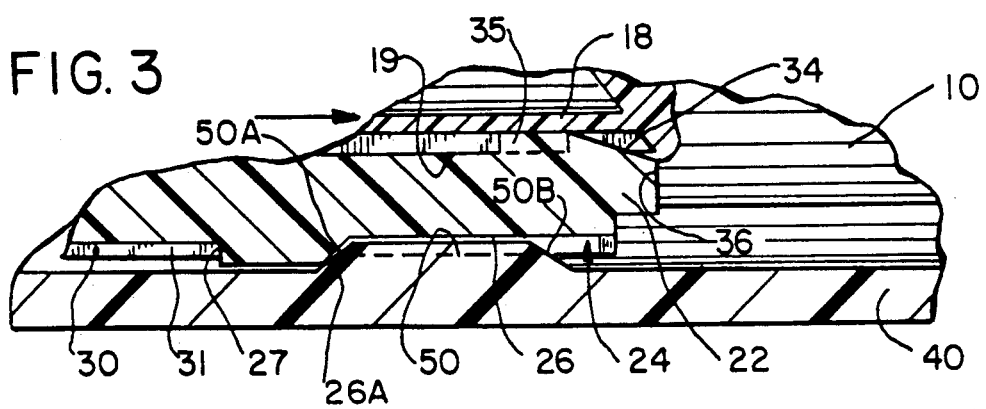
FIG. 3 is a further enlarged partial side sectional view showing details of the collar and shield.
Figure 4:
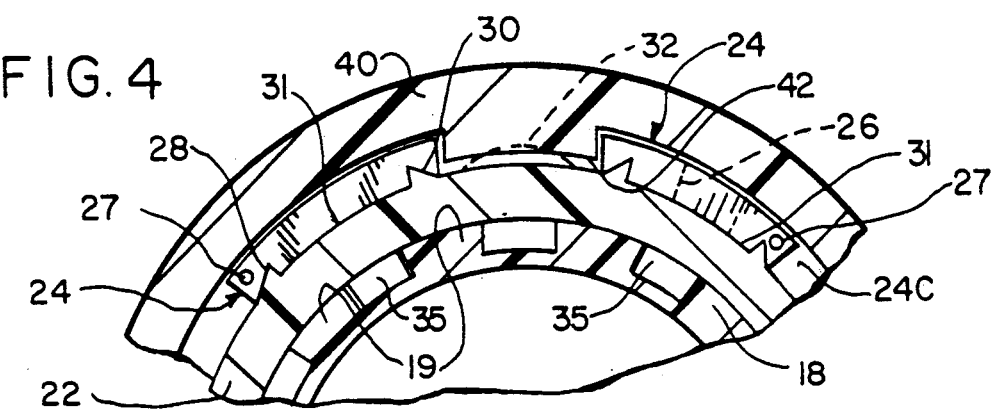
FIG. 4 is a sectional view along the line 4—4 of FIG. 2 with the shield pulled to its extended position but before rotation.

As shown most clearly in FIG. 3, the rear end of collar 22 includes a peripheral rigid tooth 34 adapted to engage the ribs 19 in the luer lock skirt 18 to retain the collar 22 on the syringe. Collar 22 is molded of a rigid plastic material such as polycarbonate resin so that when the collar is pushed over the luer lock skirt 18, the angled surface of the rigid tooth 34 allows the tooth to move over the ribs 19 until the proximal end of the collar is seated toward the distal end of the barrel with the rigid tooth 34 deforming the ribs 19 of the luer lock skirt 18 to permanently retain the collar in place on the syringe barrel 10. As an alternative, a circumferential groove may be formed in collar 22 to receive the peripheral tooth 34. This is unnecessary in the preferred embodiment in which the yieldable ribs 19 cold flow into the configuration shown in FIG. 3 but may be desirable in the case of syringes which do not include ribs molded on the exterior surface of the luer lock skirt. Instead of mechanically interlocking the collar 22 and barrel 10, other fastening means such as sonic welding or adhesives may be used within the scope of the invention, although such techniques are generally disadvantageous because of the additional steps involved and other problems which may arise with the preferred assembly techniques. The diameter of collar 22 as measured in the area of the keyways 25 is greater than the outer diameter of the syringe barrel 10 adjacent the collar.

Figure 7:
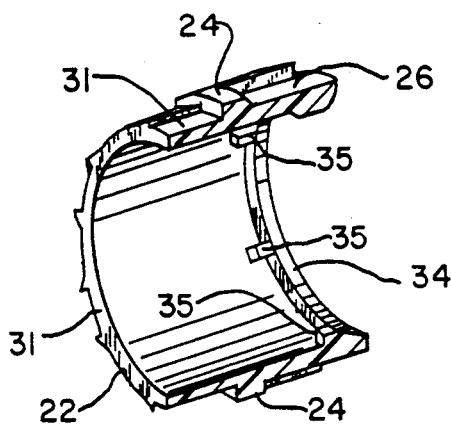

Locking lip 34 will bite sufficiently into the outer surface of the luer skirt 18 to prevent axial movement of collar 22 but in some cases slight rotation or rocking of the collar may occur. To prevent this, the tooth 34 may be formed with gaps (not shown) so that not all of the ribs 19 on the outside of the luer lock skirt 18 will be deformed. The non-deformed ribs 19 falling into the gaps resist rotation or rocking of the collar 22 relative to barrel 10. Alternatively, as shown in FIGS. 3 and 7, the inner surface of collar 22 may be provided with lugs 35 molded on the inside of the collar and adapted to fit between the ribs 19 on the outside of the luer lock skirt 18 to prevent positively any rotational movement with the meshed ribs 19.

The needle shield comprises an elongated plastic cylinder 40 (e.g., made of polypropylene) having three keys 42 integrally formed on its interior surface. An end rim 44 is formed at the proximal end of shield 40. As shown in FIG. 2, end rim 44 is adapted to abut against the proximal end of collar 22 to limit the forward movement of the shield. Each of the keys 42 includes a distal triangular point 46 and extends from the distal end of the shield to a point just short of the distal point of the triangular protrusions 24 on collar 22 when the shield is in its extended position as shown in FIG. 2. End rim 44 includes three cutout sections 45 which align with each of the keys 42. Cutout sections 45 facilitate the process for molding keys 42 but serve no functional purpose after the device has been assembled. At their rear ends, the keys 42 terminate in flat surfaces 48. With the three keys 42 in the keyways 25 in the retracted position (FIG. 1), rotational movement of the shield 40 is prevented by abutment of the edges of keys 42 against the side surfaces 24C of protrusions 24; therefore, torque can be applied to the needle while holding shield 40 to thread (or unthread) needles onto (or from) the syringe. This cannot be done with constructions in which a shield rotates freely with respect to the syringe.

Three detents 50 are also formed on the inner surface of the shield 40 toward its forward end. The detents 50 may be equally spaced and are adapted to be received within the slots 26 in the triangular protrusions 24 to retain the shield 40 in its retracted position (FIG. 1). In the preferred embodiment, as shown in the drawings, the detents 50 are each spaced thirty degrees from an adjacent key 42. It is not necessary that the detents be equally spaced. Each of the detents includes a sloped distal surface 50A and a proximal surface 50B more gradually sloped than slope 50A.

In the retracted position, the distal end of shield 40 terminates at the same point as the distal end of collar 22. An end cap 52 (see FIG. 2) is placed on the forward end of the shield 40. Cap 52 is molded from a resilient plastic material (such as polyallomer) and includes a side wall 53 and an end wall 54 which is adapted to be positioned between the distal end of collar 22 and the proximal end of the needle sheath 20 (FIG. 1) for substantially closing the distal end of shield 40. Side wall 53 is shaped as shown so that end cap 52 can be retained on shield 40 by the interlocking mechanical engagement of the side wall 53 and a complementary projection 55 at the forward end of shield 40. Cap 52 need not be a separate part and can, instead, be formed as an integral part of shield 40.

The end wall 54 includes a central needle aperture which is made small enough that the end of shield 40 is closed to the maximum extent while allowing the locking ears 16A of needle hub 16 to be extended through the aperture to permit needles to be mounted and removed while the shield 40 is in its retracted position (FIG. 8). The aperture is not, however, large enough to allow the proximal end of the sheath to pass through it. The minimum needle aperture reduces the likelihood that a child or person with small fingers may accidentally contact the needle point. End cap 52 also makes the distal end of shield 40 more rigid and resistive to deformation when dropped or otherwise impacted upon a hard surface.

In addition, the rim 54 and its position between the proximal end of needle sheath 20 and the distal end of barrel 10 serves a functional purpose when removing or installing needles on the luer tip 17 (FIG. 8), for example, when the filling and injection needles are different. When a needle is to be mounted on a syringe, the syringe is held by shield 40 with the shield in its retracted position. Needle hub 16, projecting from the proximal end of the protective sheath 20, is inserted through the aperture in the end wall 54 and the hub telescoped onto the luer tip 17. Using the conventional cooperative wrenching tabs (not numbered) of the sheath and needle, the needle hub 16 is rotated by twisting and pushing with the sheath to thread the locking tabs 16A within the internal threads 18A in the luer skirt 18 until needle 14 is mounted on the syringe. As hub 16 is threaded onto the luer tip 17, the needles move axially relative to sheath 20. The shield 40 is prevented from rotating by abutment of keys 42 against surfaces 24C of protrusions 26, while the rim 54 provides a surface against which the needle sheath can be forced. Without this feature, the user could not grasp the shield alone when installing and removing the needle since the force exerted by the needle hub on the syringe luer tip would push the syringe out of the shield. This would mean that the user would have to remember to grasp the barrel and not the shield when removing and attaching the needle.

Figure 9:
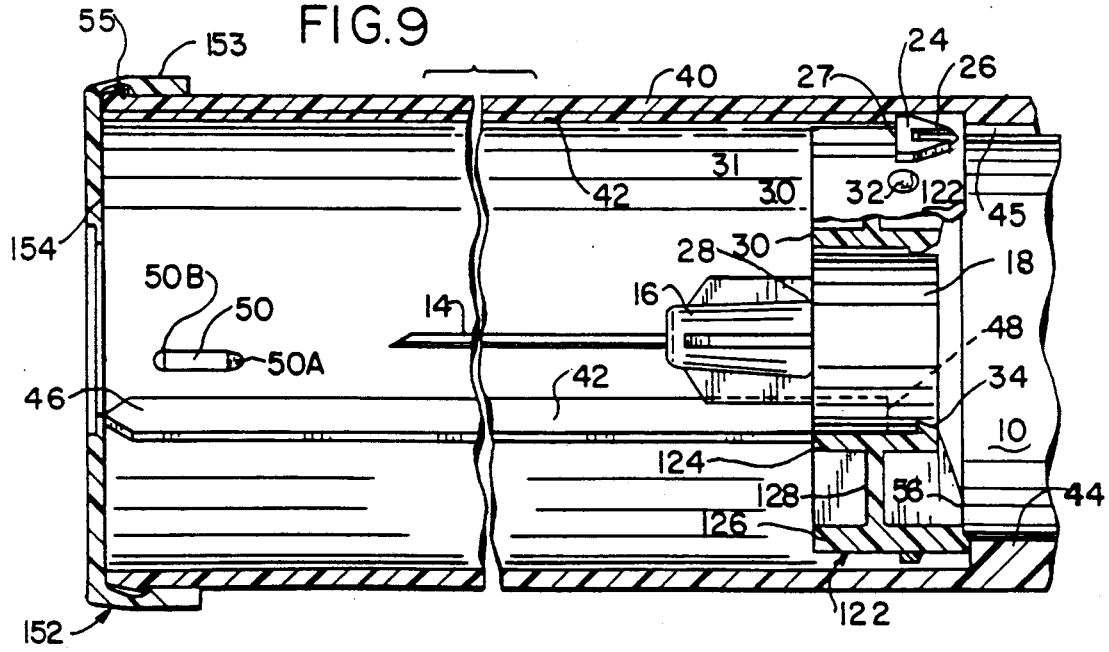
FIG. 9 is an enlarged side sectional view showing a shield in its extended position relative to the collar of FIG. 8.

The end wall 54 is particularly important when the invention is used in conjunction with large diameter barrels. Such a construction is shown in FIGS. 8 and 9 wherein like numerals are used to identify parts identical to those shown in the embodiment of FIGS. 1–6. In FIGS. 8 and 9 the needle 14 and hub 16 are the same as in FIG. 1 as is the luer tip 17 and the luer lock skirt 18. In this case, however, the collar 122 includes two concentric hubs or sleeves 124 and 126 supported by an annular strut 128 preferably forming an I-beam in cross-section as shown in FIG. 9. The cross-sectional shape is not critical, however, and those skilled in the art will readily understand that the cross-section could be cup- or channel-shaped, with a web extending either distally or proximally between the concentric hubs or sleeves. The end cap 152 includes side wall 153 and end wall 154 which, as shown, covers a substantial portion of the barrel opening and thus greatly reduces the risk of accidental needle stick when the shield is in its extended position.

The device may be assembled as follows. Shield 40 is inserted on the forward end of the barrel 10 of an assembled syringe to its retracted position shown in FIG. 1 (prior to installation of the needle 14 and sheath 20 on the syringe). With the shield 40 held in position, the collar 22 is then placed over the luer lock skirt 18 inside of the shield 40. Engagement of the triangular protrusions 24 on collar 22 with the triangular points 46 at the end of keys 42 on shield 40, as the collar 22 is pushed onto the luer lock skirt 18, causes the shield 40 to rotate until the keys 42 are positioned in the keyways over detents 32 between adjacent triangular protrusions 24. The collar 22 is pushed inwardly until the proximal end of the collar butts up against the face 56 on the syringe barrel 10. In this position, as shown in FIG. 3, the three detents 50 are seated in the slots 26 of three of the protrusions 24. After the shield 40 and collar 22 have been assembled on the syringe, end cap 52 is placed on the shield 40. The needle 14 with its sheath 20 may then be attached to the luer tip to complete the assembly.

Alternatively, collar 22 may be positioned within shield 40 with the keys 42 positioned in the appropriate keyways 25. The shield and collar may then be telescoped together over the syringe barrel with the collar being forced onto the luer lock skirt as the shield is moved to the retracted position in which the proximal end of the collar abuts against the distal face of the syringe barrel. This procedure, with appropriate tooling, may be used with the end cap 52 in place on the shield which means that this assembly process could be used with a shield having end wall 54 integrally formed as a portion of the shield as mentioned above. Conversely, this alternative assembly method can be used with an open shield in which case end cap 52 can be placed on the shield after assembly.

The use of the syringe may be conventional. Needle sheath 20 is removed and medication drawn into barrel 10 by withdrawal of plunger 12 with the shield in its retracted position shown in FIG. 1. After the contents of the syringe have been injected into a patient, the shield 40 is pulled forward into the extended position shown in FIG. 2. When this happens, the keys 42 slide in the keyways 25 over detents 32 between the adjacent protrusions 24 on collar 22 (FIG. 4) and the distal surface 50A of detents 50 slide over surface 26A (FIG. 2) of slots 26. The user can feel the rear edges 48 of keys 42 clearing detents 32, which signals that the shield 40 is fully extended.

Figure 5:
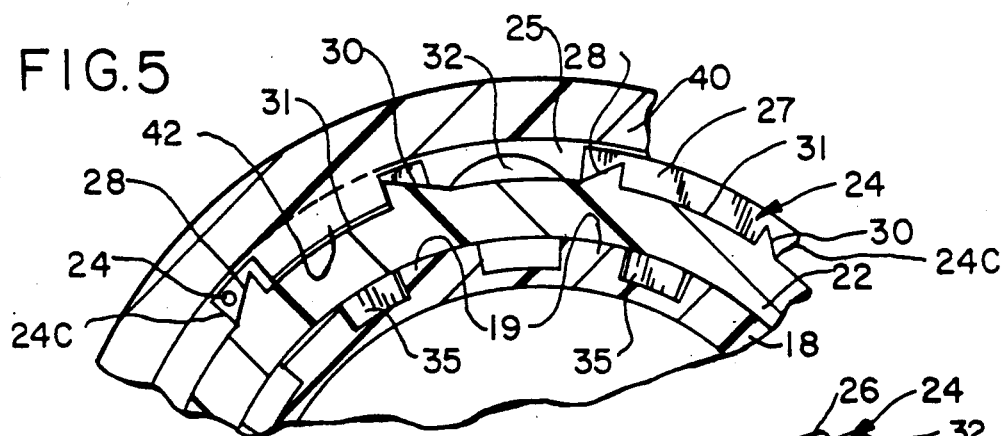
FIG. 5 is a sectional view along the line 4—4 of FIG. 2 showing the shield rotated into its locked position.

To lock the shield in place, the user rotates shield 40 causing the keys 42 to move over the adjacent ramps 28 (or 30) until the key fall into the locking slots 31 formed between each pair of ramps 28 and 30 (see FIG. 5). Because of the arrangement of the ramps 28 and 30, the shield can be locked by rotating it either clockwise or counterclockwise. When the keys 42 are positioned in the locking slots 31, the rear edge 48 of each key abuts against the squared off surface 27 of one of the triangular protrusions 24 so that the shield cannot be returned to its retracted position without application of excessive force. Because of the interlocking relationship of the square key and locking slots, shield 40 can no longer be rotated and, accordingly, the shield is permanently locked in place.

There are circumstances where it may be desirable to extend the shield 40 to the position shown in FIG. 2 without locking it in place. For example, if a syringe is to be filled at a location remote from the patient, rather than replacing the sheath 20 after the syringe is filled, it is preferable to extend shield 40 so that it functions as a temporary protective element while the syringe is carried to the patient. Use of the protective shield 40 in this fashion is facilitated by the detents 32 on collar 22. These detents 32 are positioned in each of the keyways 25 between the triangular protrusions 24 so that when the shield 40 is pulled to its extended position (FIG. 2), the flat end 48 of each of the keys 42 abut against one of the detents 32. This prevents the shield 40, when it is in its extended position, from being retracted unless sufficient force is applied to move the keys 42 over the detents 32. Hence, in this situation, the shield is first extended as a temporary sheath for the needle, returned to its retracted position for the patient's injection, and then finally again extended and locked by rotation so that the shield cannot be retracted. If it is desired to return the shield 40 to its retracted position rather than locking the shield in its extended position, because of the gradual slope of surface 50B of detent 50, the detent can be pushed over the squared off surface 27.

What is claimed is:

1. In combination, (a) a syringe comprising a barrel having distal and proximal ends, a plunger slidable within the barrel, and a needle attached to the distal end of the barrel, (b) a collar having distal and proximal ends at the distal end of said barrel and including a plurality of locking slots on its outer surface, each of said locking slots being formed by a pair of opposing walls on the distal portion of said collar and a protrusion at the back of the locking slot extending along the proximal portion of said collar, at least one of said pair of opposing walls including a ramp shaped wall surface thereon, (c) an elongated needle shield movable over said barrel and collar between a retracted position in which the needle is exposed and an extended position in which said shield covers said needle, said shield including a plurality of elongated keys on its interior surface, each of said keys having distal and proximal ends and being adapted to slide in a keyway displaced circumferentially from said locking slots and wherein at least one of said keys on said shield is rotatable over said wall surface into at least one of said locking slots when said shield is in its extended position, and (d) retaining means on said collar and shield for retaining said shield in its retracted position.

2. In combination:

(a) a syringe comprising a barrel, a plunger slidable within the barrel, and a needle attached to the forward end of the barrel, (b) a collar at the forward end of said barrel and including a plurality of locking slots on its outer surface, each of said locking slots being formed by a pair of opposing walls on the forward portion of said collar and a protrusion at the back of the locking slot, at least one of said pair of opposing walls including a ramp shaped wall surface thereon, (c) an elongated needle shield movable over said barrel and collar between a retracted position in which the needle is exposed and an extended position in which it covers said needle, said shield including a plurality of elongated keys on its interior surface, each of said keys being adapted to slide in a keyway displaced circumferentially from said locking slots and wherein at least one of said keys on said shield is rotatable over said wall surface into at least one of said locking slots when said shield is in its extended position, and (d) a retaining means on said collar and shield for retaining said shield in its retracted position, and wherein each of said opposing walls includes a ramp shaped wall surface so that each of said keys can be rotated in either direction into said locking slots.

3. The combination according to claim 1, wherein said retaining means on said shield includes at least one detent on its interior surface and said retaining means on said collar includes a surface member adapted to abut against said detent to retain said sleeve in its retracted position.

4. The combination according to claim 1, wherein said collar includes at least one detent on its outer surface adapted to operatively contact the proximal end of at least one of said keys when said shield is in its extended position.

5. The combination according to claim 1, wherein said needle includes a hub at its proximal end and a protective needle sheath and wherein said shield includes an end wall at its distal end, said end wall including an aperture large enough to permit the hub of the needle to pass therethrough for mounting and removing the needle but not large enough to permit the proximal end of the sheath to pass therethrough.

6. The combination according to claim 1, wherein said shield includes an inwardly extending rim at its proximal end adapted to abut against the proximal end of said collar to limit the forward movement of said shield as said shield is moved to the extended position.

7. The combination according to claim 1, wherein each of said protrusions is tapered toward the proximal end of the collar, said protrusions being equally spaced with the space between adjacent protrusions comprising a keyway through which said keys can slide and wherein the distal end of each of said keys is tapered in shape, whereby when said collar is inserted into the shield during assembly, the tapered distal end of said keys cause said shield to be positioned such that each of said keys lies in one of said keyways.

8. The combination according to claim 5, including means for preventing rotation of the needle shield when the needle shield is in the retracted position.

9. The needle shielding device according to claim 8, wherein said means for preventing rotation of the needle shield also prevents said rotation when the needle shield is in any position other than the extended position.

10. The combination according to claim 8, wherein said means for preventing rotation comprises projections extending from the exterior surface of said collar.

11. The combination according to claim 1, wherein said collar is separate from said barrel and wherein there is provided means for securing said collar to said barrel and interlocking means on said collar and barrel for preventing rotation of said collar.

12. The combination according to claim 5, wherein said end rim lies between the proximal end of the needle sheath and the distal end of the collar when the needle shield is retracted and further including means for preventing rotation of said needle shield when it is in its retracted position.

13. The needle shielding device according to claim 12, wherein said means for preventing rotation of the needle shield also prevents said rotation when the needle shield is in any position other than the extended position.

14. The combination according to claim 3, wherein said detent includes distal and proximal surfaces and the proximal surface of said detent is sloped so that said detent can be pushed over said protrusion to return the shield from its extended unrotated position to the retracted position.

15. In combination,
(a) a syringe comprising a barrel, a plunger slidable within the barrel, and a needle attached to the forward end of the barrel,
(b) a collar attached to the forward end of said barrel, said collar including a plurality of locking slots rectangular in cross-section on its outer surface, each of said locking slots comprising a pair of opposing walls each in the form of a ramp, said collar further including and a triangular protrusion at the proximal end of and terminating the locking slot, the apex of each triangular protrusion extending proximally, with at least one protrusion including a detent slot,
(c) an elongated needle shield movable over said barrel and collar between a retracted position in which the needle is exposed and an extended position in which it covers said needle, said shield including a plurality of elongated keys on its interior surface, each of said keys being substantially rectangular in cross-section and including a triangular shaped front end and being adapted to slide in a keyway between said protrusions, each of said keys being rotatable into a locking slot over one of said ramps when said shield is in its extended position, and
(d) at least one detent on said shield for retaining said shield in its retracted position when it is positioned in one of said at least one detent slots in said protrusions.

16. The combination according to claim 15, wherein said collar includes at least one detent on its outer surface positioned to abut against the rear edge of at least one of said keys when said shield reaches its extended position.

17. The combination according to claim 16, wherein said shield includes a cap having an annular rim at its forward end.

18. The combination according to claim 15, wherein said shield includes an inwardly extending rim at its proximal end adapted to abut against the proximal end of said collar to limit the movement distally of the shield.

19. The combination according to claim 15, including means for preventing rotation of the needle shield when the needle shield is in the retracted position.

20. The needle shielding device according to claim 19, wherein said means for preventing rotation of the needle shield also prevents said rotation when the needle shield is in any position other than the extended position.

21. The combination according to claim 19, wherein said means for preventing rotation comprises projections on the exterior surface of said collar.

22. The combination according to claim 15, wherein there is provided means for securing said collar to said barrel and interlocking means on said collar and barrel for preventing rotation of said collar.

23. The combination according to claim 15, wherein said needle is covered by a needle sheath and said end rim lies between the proximal end of the needle sheath and the distal 24. The needle shielding device according to claim 23, wherein said means for preventing rotation of the needle shield also prevents said rotation when the needle shield is in any position other than the extended position.

25. The combination according to claim 23, wherein the proximal surface of said detent is sloped so that said detent can be pushed over said protrusion to return the shield from its extended unrotated position to the retracted position.

26. A medical device comprising, in combination:
a barrel having distal and proximal ends;
a needle extending from the distal end of said barrel and terminating in a point;
a shield longitudinally movable on said barrel between a retracted position in which the needle is exposed and an extended position in which the needle point is covered;
means on the barrel and shield for rotationally orienting the shield on the barrel in at least one unlocked and extended position when the shield is moved longitudinally to the extended position;

means on the barrel and shield, responsive to rotation of the shield on the barrel from the unlocked and extended position to a locking position, for preventing rotation of the shield on the barrel to the unlocked and extended position;

stop means being disposed on the barrel and shield so that when the shield is in the extended, locked position the stop means are aligned for abutment to prevent movement of the shield toward the retracted position and when the shield is in the extended, unlocked position the stop means are not aligned for abutment, thereby allowing movement of the shield toward the retracted position;

wherein said stop means includes (a) at least one locking slot defined by a pair of opposing walls on the barrel and a protrusion at the proximal end of the locking slot and (b) at least one elongated key on the interior surface of the shield, said key being rotatable over said ramp into said locking slot, and wherein each of said opposing walls includes a ramp so that said key can be rotated in either direction into the locking slot.

27. In combination,
(a) a syringe comprising a barrel, a plunger slidable within the barrel, and a needle attached to the forward end of the barrel,
(b) a collar attached to the forward end of said barrel, said collar including at least one locking slot on its outer surface, said at least one locking slot comprised of a pair of opposing walls at least one of which is in the form of a ramp, said collar further including a plurality of protrusions at the proximal end of said locking slot,
(c) an elongated needle shield movable over said barrel and collar between a retracted position in which said needle is exposed and an extended position in which said shield covers said needle, said shield including at least one elongated key on its interior surface, said at lest one key being substantially rectangular in cross-section being adapted to slide in a keyway between said protrusions, said at least one key being rotatable into a locking slot over one of said ramps when said shield is in its extended position, and
(d) at least one detent on said shield for retaining said shield in its retracted position when said at least one detent is positioned adjacent one of said protrusions.

28. A method of assembling a safety syringe, comprising placing a protective shield having one or more elongated keys on its interior surface over the distal end of a syringe and then inserting a cylindrical collar having locking slots and keyways between the locking slots between the shield and the barrel of the syringe and positioning the shield relative to the collar so that the keys fall within the keyways on the collar and then securing the collar to the shield and syringe.

29. A method of assembling a safety syringe according to claim 28, wherein the keys of the shield are caused to fall within the keyways in the collar by moving the shield in an axial direction relative to the collar.

30. A method of assembling a safety syringe comprising placing a protective shield having one or more elongated keys on its interior surface over a cylindrical collar having locking slots and keyways between the locking slots such that the protective shield is operatively positioned with respect to the cylindrical collar and the combination of the shield and collar together are then pushed onto the barrel of a conventional syringe.

* * * * *